(12) United States Patent
Mcclymont et al.

(10) Patent No.: US 9,597,093 B2
(45) Date of Patent: Mar. 21, 2017

(54) TEMPORARILY FIXABLE ANGLED DRILL

(71) Applicant: Howmedica Osteonics Corp., Mahwah, NJ (US)

(72) Inventors: Kaitlin Elizabeth Anne Mcclymont, Hoboken, NJ (US); Andrew Nelson, Tinton Falls, NJ (US); Nicholas Olson, Bloomfield, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/300,547

(22) Filed: Jun. 10, 2014

(65) Prior Publication Data

US 2015/0354635 A1 Dec. 10, 2015

(51) Int. Cl.
| | | |
|---|---|---|
| *A61B 17/80* | (2006.01) | |
| *A61B 17/16* | (2006.01) | |
| *B23B 39/14* | (2006.01) | |
| *B23B 45/00* | (2006.01) | |
| *F16D 3/26* | (2006.01) | |

(52) U.S. Cl.
CPC .......... *A61B 17/1631* (2013.01); *B23B 39/14* (2013.01); *B23B 45/003* (2013.01); *F16D 3/265* (2013.01); *Y10T 408/66* (2015.01)

(58) Field of Classification Search
CPC . F16D 3/16; F16D 3/265; A61B 17/16; A61B 17/1631; B23B 39/14; B23B 45/003; B25B 7/06; Y10T 403/32311; Y10T 408/66
USPC .......... 464/120; 403/90; 606/80; 81/177.75; 74/529, 537; 269/2, 89
See application file for complete search history.

(56) References Cited

U.S. PATENT DOCUMENTS

| | | | | |
|---|---|---|---|---|
| 290,103 | A | * | 12/1883 | Paul ............................ 403/90 X |
| 700,369 | A | * | 5/1902 | Pixley ........................... 464/120 |
| 952,435 | A | * | 3/1910 | Miller .................... 81/177.75 X |
| 1,499,862 | A | | 7/1924 | Eichenberg |
| 2,865,240 | A | * | 12/1958 | Kniser ........................ 269/89 X |
| 3,448,592 | A | | 6/1969 | Pool et al. |
| 4,673,376 | A | * | 6/1987 | Fender ........................ 403/90 X |
| 5,219,174 | A | | 6/1993 | Zurbrugg et al. |
| 5,236,289 | A | * | 8/1993 | Salyer .................... 81/177.75 X |
| 5,464,407 | A | | 11/1995 | McGuire |
| 5,515,754 | A | | 5/1996 | Elkins |
| 6,102,134 | A | | 8/2000 | Alsruhe |

(Continued)

FOREIGN PATENT DOCUMENTS

CH 157799 * 10/1932 ...................... 403/90

*Primary Examiner* — Gregory Binda
(74) *Attorney, Agent, or Firm* — Lerner, David, Littenberg, Krumholz & Mentlik, LLP

(57) ABSTRACT

A drive tool has a tubular drive shaft extending along a first axis with a first end of the shaft defining a connector element including a part-spherical cavity. A second end of the shaft has a drive element. The connector element has walls surrounding the part-spherical cavity, and a pair of slots extending along the walls of the connector element between an outer surface of the connector element and the cavity. A drive element extends along a second axis having a driver tool at a first end and a part-spherical head at a second end, the head pivotally mount in the part-spherical cavity in the connector element. A pair of deflectable arms which engage the part-spherical head are mounted adjacent the cavity of the tubular drive shaft and are deflectable through the slots onto the part-spherical head.

16 Claims, 21 Drawing Sheets

(56) References Cited

U.S. PATENT DOCUMENTS

| | | | |
|---|---|---|---|
| 6,105,473 | A | 8/2000 | Huang |
| 6,347,564 | B1 | 2/2002 | Ciocca |
| 6,386,074 | B1 | 5/2002 | Yang |
| 6,776,499 | B2 | 8/2004 | Chang |
| 7,278,342 | B1 | 10/2007 | Chang |
| 7,503,921 | B2 * | 3/2009 | Berthusen et al. ............ 606/80 |
| 7,597,031 | B2 | 10/2009 | Chiang |
| 7,927,036 | B2 * | 4/2011 | Reasoner ................ F16G 11/10 403/90 X |
| 8,215,208 | B2 | 7/2012 | Blackston et al. |
| 9,080,611 | B2 * | 7/2015 | Sander |
| 2006/0260446 | A1 | 11/2006 | Chang |
| 2008/0012245 | A1 | 1/2008 | Peters |
| 2012/0143195 | A1 | 6/2012 | Sander |

\* cited by examiner

TEMPORARILY FIXABLE ANGLED DRILL

BACKGROUND OF THE INVENTION

The present invention relates to a driving or cutting tool, and more particularly to a driving or cutting tool having a rotatable connection device for rotatably connecting a tool, a fastener, a work piece or a driven member to a driveshaft. The rotatable connection device allows the tool shank, fastener, work piece or the driven member to be selectively secured to the tool driveshaft and to be rotated or driven by the driveshaft and be selectively tiltable or slantable relative to the driveshaft axis while rotating.

Typical driving tools, such as wrenches or screwdrivers, may comprise a connector attaching a drill tool member, a tool bit, a fastener or a work piece in a manner to allow the tool bit, fastener, etc. to be selectively secured to a driveshaft and rotated in concert with the driveshaft and to be tiltable or slantable relative to the driveshaft.

Rotational drivers such as drills or screwdrivers having a pivoting mechanism to allow a drill or other tool to be driven at an angle relative to a driver axis are well known. Some of these tools provide an upper angular limit for the angle of the axis of the driven tool to the axis of the driveshaft. Many drive tools provide a method of locking the tool at this maximum angle and also locking the tool when the axis of the drive tool is parallel or collinear with the axis of the driveshaft.

BRIEF SUMMARY OF THE INVENTION

It has been found, especially in surgical applications, that providing the ability for adjusting the maximum angle of the driveshaft axis to the driven tool axis, for example, 45° to 0° (coaxial), continuously or at relatively small discrete increments provides various advantages. The more the angle is between shaft and drill bit axis, the less stable the bit is on the surface to be drilled. Also, increasing this angle increases the difficulty in applying a force in-line with the bit axis of rotation thus making the drilling operation more difficult (especially in case with hard sclerotic bone). Ideally, the shaft should be in-line with the axis of the cutting attachment, but anatomical limitations and exposure difficulties often prevent this. Allowing incremental angle adjustments allows for maximizing the downward (axial) force component under these circumstances. For example, during a drilling operation onto bone, the initial drilling can take place at an angle between the driveshaft and the drill bit of, for example 45° and then gradually and continuously change to 0°, when the axis of the drive shaft and driver tool are collinear, so that the force can be applied in-line with the axis of rotation of the bit and in direction of cutting (i.e. downward).

This ability may be provided by a tool connection or coupling device which has a first member extending along a first axis, which first member has an internal cavity adjacent a first end of the first member and has a threaded outer surface. The tool has a second member extending along a second axis having a driver member such as a drill or screwdriver at a first end and a joint element at a second end. The joint element of the second member is pivotally mounted in the cavity of the first member. The joint may be a ball and socket joint and/or universal joint.

The second member has an angled surface intermediate the first and second ends, the angled surface angled outwardly in a direction from the second to the first ends i.e. from adjacent the joint to a wider portion adjacent the drill or driver. A sleeve having a threaded inner bore is mounted on the threaded outer surface of the first member and is capable of moving along the first axis toward and away from the angled surface of the second member. The sleeve has a leading tapered end for contacting the angled surface of the second member. The sleeve on the first member is movable to multiple positions along the first axis via rotation on the engaged threads. Each position allows for an angle between the second axis and the first axis to be limited to any angle between, for example, 0 and 45°. Obviously, larger or smaller angles can be provided by varying the angle of the tapered portion on the sleeve or the angled portion on the second member in the area where they contact.

In one embodiment of the present invention, the cavity of the first member has a pivot pin extending therethrough in a direction perpendicular to the first axis. The second end of the second member has a bore therethrough for receiving the pivot pin. The second end of the second member may be generally spherical such as a ball joint or it might be a u-joint or use gears (bevel, etc.). When a ball joint is used the bore extends through an equatorial region of the spherical second end portion in a direction generally perpendicular to the second axis. The bore may intersect a pair of grooves in the outer circumference of the spherical portion which grooves extend generally parallel to the second axis. The grooves allow rotation of the second end of the second member in a direction parallel to the axis of the pivot pin.

The rotation element of the second member includes a part-spherical outer surface and the first member cavity includes a part-spherical inner surface. A part-spherical outer surface of the rotation element rotates on the part-spherical inner surface of the first member as the second element is rotated about the pivot pin either along the pivot pin axis or at a angle to the pivot pin axis when the second member is rotated so that part of the grooves in the rotation element contact the pin.

The angled surface of the second member, which tapers outwardly from the second end to the first end thereof, may taper at an angle of approximately 45°. The angled surface can be in the form of a frustro-conical body of rotation utilizing the 45° angle. Other angles could also be used. The first end of the second member can include a cutting tool such as a drill, an awl, a burr, and a reamer as well driving tools such as a screw or nut driver. These tools may be coupled to the second member in any known manner.

The first member is driven by a power tool such as an electric or pneumatic power tool or by hand. The driveshaft itself may be either solid or may be flexible. The sleeve is threaded onto the threads of the first member and may include a releasable detent system for holding the sleeve in a desired rotational position on the first member. The detent system can provide a desired limit to the movement of the sleeve along the first axis and thus the relative rotation between the first and second member with respect to the first and second axes.

The first embodiment described can be used for drilling a hole in a bone by mounting a drill bit in the first end of the second member and then inserting the drill mounted on the first end of the second member into bone at a desired angle usually between 0 and 45° or up to 75° with the sleeve holding the axis of the second member at the desired angle between 0 and 75° with respect to the axis of the first member. As drilling progresses, the sleeve is rotated in a manner to move the sleeve along the first member toward the second member to gradually reduce the angle between the first member and second member until the first and second axes are collinear. At this point, the angle between the first and second axis is 0°. If a detent system is used on the sleeve the advance can be step wise rather than continuously with the detent allowing, for example, 5° steps.

In a second embodiment, the tool is a variation/improvement stemming from the Stryker (assignee of the present application) publication US 20120143195 A1. It is a drill shaft with a continuously variable angle drill bit. The drill bit has a ball that sits in the socket of the shaft. The shaft transmits torque to the ball through a pin. It improves upon US 20120143195 by removing the threaded ferrule or threaded sleeve for reduced bulk and by providing a means, such as deflectable fingers, arms or tabs to apply friction between the ball of the drill bit and the socket of the shaft. The purpose of applying this friction is to maintain the angle of the bit or driver relative to the shaft to allow for easy insertion through the surgical incision. As with the first embodiment the part-spherical head has a cross-bore therethrough and is mounted on a pivot pin fixed to the socket.

The drill shaft may be manufactured with an undersized socket and one or more deflectable tabs, preferably two, may be formed with the combination of a center bore of the drive and electro discharge machined (EDM) wire cuts through the wall of the shaft. The tabs are then bent inwardly into the socket formed at the end of the shaft. Alternatively, the socket and tabs can be machined into a geometry that not require subsequent bending. Upon assembly the tabs provide a constant friction fit within the socket to the part-spherical head of the bit or driver.

The socket is shaped to match the head of the drill or other tool. The drill shaft may be manufactured with a to-size socket i.e. a sliding fit between the part-spherical head and socket, and one or more tabs, preferably two, may be formed with the combination of the center shaft bore and EDM wire cuts. These tabs will have "buttons" (or raised pressure points) near the handle of the shaft, preferably a distance from the bit. Applying pressure to these tab buttons will apply a temporary friction fit between the shaft cavity and the bit head.

The deflectable tabs are suitable for creating a force on the sides (i.e. orthogonal to the shaft) of the ball of the drill bit. Alternatively, a force can be applied to the top and/or bottom (i.e. in line with the shaft axis) of the ball of the drill bit. This force could be provided continuously with a spring (for example, a coil spring), intermittently through direct mechanical manipulation, or intermittently by using mechanical manipulation to control the spring. If a force is applied to the top &/or bottom of the ball of the drill bit, then the frictional force that will serve to restrict motion of the drill bit would occur between the pin passing through the ball and the saddle-shaped recess inside the ball.

It is desirable that the inner contour of the tabs is spherical/circular and that this contour covers a portion of both hemispheres of the part-spherical drill bit head. This is so that when the user "pinches" the ball with the tabs the pressure is applied from the side, not from solely the bottom or the top. Applying force from solely the bottom or the top may force the friction fit to occur between the pivot pin and the drill bit, not the shaft socket inner part-spherical cavity and the part-spherical drill bit head. If the friction fit occurs between the pin and the drill bit head top or bottom, the bit may want to toggle into a different position. The ability to toggle into a preferred position can be an advantage, and if the preferred position is not axially aligned with the shaft then the seat and ball can be configured such that the drill bit default position is at some axis to the shaft.

Various aspects of the present invention are provided by a drive tool which has a tubular drive shaft extending along a first axis. The drive shaft has a first end defining a connector element including a part-spherical cavity and a driver element at a second end. The connector element has walls surrounding the part-spherical cavity with a first and second pair of slots extending along the walls of the connector element between an outer surface of the connector element and the part-spherical cavity.

A pivot member extending along a second axis has a tool at a first end and a part-spherical head at a second end. The part-spherical head is pivotally mounted in the part-spherical cavity in the connector element.

At least one deflectable arm engageable with the part-spherical head is mounted adjacent the part-spherical cavity at the first end of the tubular drive shaft and deflectable through the first pair of slots into engagement with the part-spherical head.

The part-spherical head of the pivot member includes a bore therethrough along an axis perpendicular to the second axis and a pivot pin mounted on the walls of the connector element surrounding the cavity extends through the bore in the part-spherical head along an axis generally perpendicular to the first axis.

The bore in head has a pair of grooves extending from the bore parallel to the second axis to allow the head to be rotated about an axis transverse to the axis of the pin.

The tubular drive shaft includes a first and second pair of slots extending parallel to the first axis and connect to the slots in the cavity walls at a first end and wherein the arms are mounted on the tubular drive shaft at a second end of the slots, the second end of the slots is closer to the second driver end of the tubular drive shaft than to the first end of the tubular drive shaft.

The arms are fixedly connected to the tubular drive shaft at the first and second pair of slots respective second ends such as being integrally (one-piece) formed thereon such as EDM or attached by welding or riveting.

The first and second pair of slots are diametrically opposed on the tubular drive shaft. Or course, it is possible to use three or four arms or tabs formed by each pair of slots rather than two. Each arm has a raised portion adjacent the second arm end extending outwardly of an outer surface of the tubular drive shaft.

The first end of each arm or tab has a part-spherical inner surface conforming in shape to the part-spherical head of the pivot member.

Alternatively, the first end of each arm or tab could have an inner surface that does not conform to the shape of the part-spherical head. For example, the inner surface could be flat which would result in a point contact with the part-spherical head of the pivot member. The inner surface could consist of two flat surfaces oriented orthogonally to each other. Such a configuration would result in two point contacts with the head and would also serve to locate the head on the pin in a manner similar to a part-spherical inner surface. Inner surfaces consisting of at least one flat plane may be easier to manufacture and clean than part-spherical inner surfaces.

Each deflectable arm may have a raised portion at the second end extending outwardly of an outer surface of the walls of the connector element. Each deflectable arm has an inner surface conforming to the part-spherical shape of the pivot element head.

Other aspects of the present invention are provided by a drive tool having a tubular drive shaft extending along a first axis having a first end defining a connector element including a part-spherical cavity and a second driver end. The connector element has walls surrounding the part-spherical cavity, and a first and second pair of slots extending along the walls of the connector element between an outer surface thereof and the part-spherical cavity.

A bit member extends along a second axis having a tool at a first end and a part-spherical head at a second end. The head is pivotally mounted in the part-spherical cavity in the connector element.

A pair of deflectable arms engageable with the part-spherical head are, mounted adjacent the cavity of the tubular drive shaft and are each deflectable through the respective first and second slots onto the part-spherical head.

The tubular drive shaft includes a first and second pair of slots extending parallel to the first axis which are connected to the slots in the cavity walls of the tubular drive shaft first end. The arms are mounted at a second end of the slots, the second end of the slots being closer to the second drive end of the tubular drive shaft.

The arms are fixedly connected to the tubular drive shaft at each of the slots respective second ends.

DETAILED DESCRIPTION

Figure 1A:
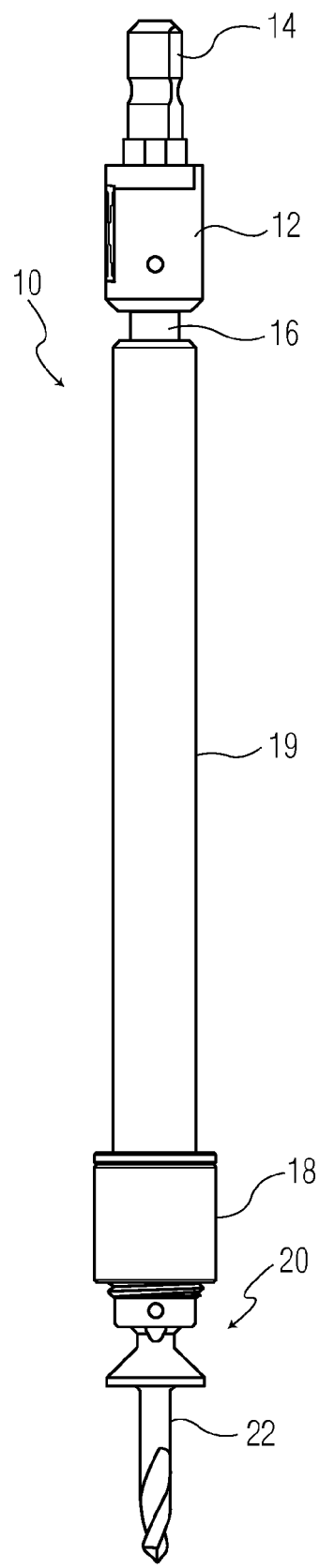
FIG. 1A is a first elevation view of a tool utilizing the connecting device of the present invention.
Figure 1B:
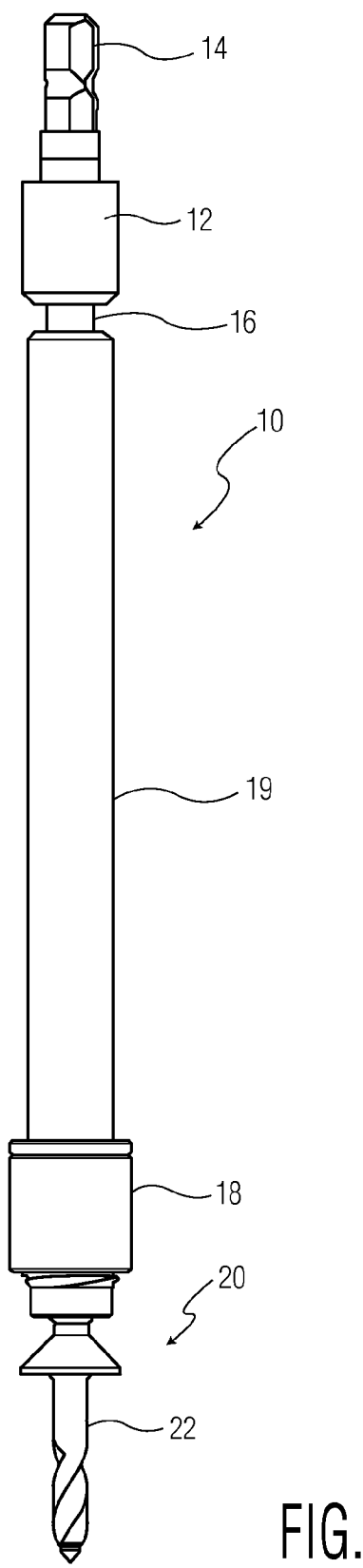
FIG. 1B is a second elevation view of the tool of FIG. 1 with the shaft of the tool rotated 90° about a longitudinal axis.

Referring to FIGS. 1A and 1B there is shown a first embodiment of a drive tool generally denoted as 10 having a first driven end 12, including, for example, a drive element 14, adapted to be received in the chuck of an electric or pneumatic power tool or a tool driven by hand. Rotation of the drive element 14 drives a shaft 16, which may be either solid or flexible. The drive tool 10 includes a second end 18, including a connection element generally denoted as 20, which connects a tool, such as, for example, drill bit 22 to drive shaft 16. A freely rotatable sleeve 19 is mounted on shaft 16 to permit a user to hold the sleeve and guide tool 10. Thus a user can hold sleeve 19 stationary while shaft 16 rotates within a hollow bore of sleeve 19.

Figure 2:
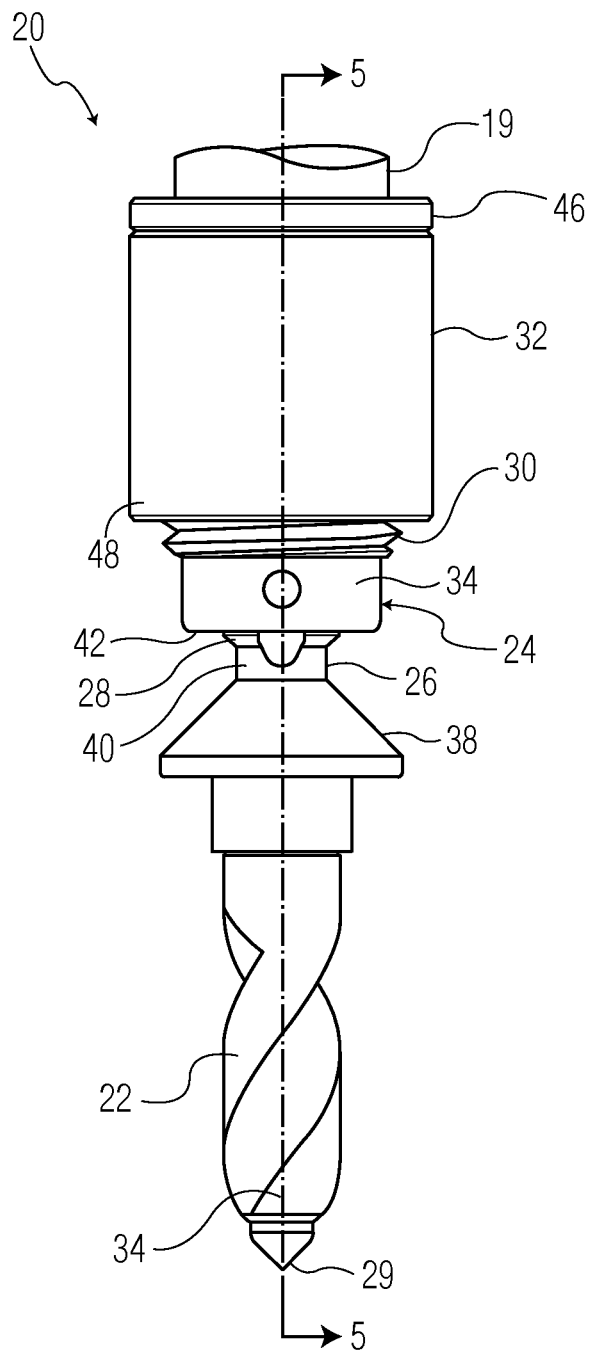
FIG. 2 is an enlarged view of the driving end of the tool of FIGS. 1A and 1B with the connecting device of the present invention showing a sleeve thereon in a first position.
Figure 3:
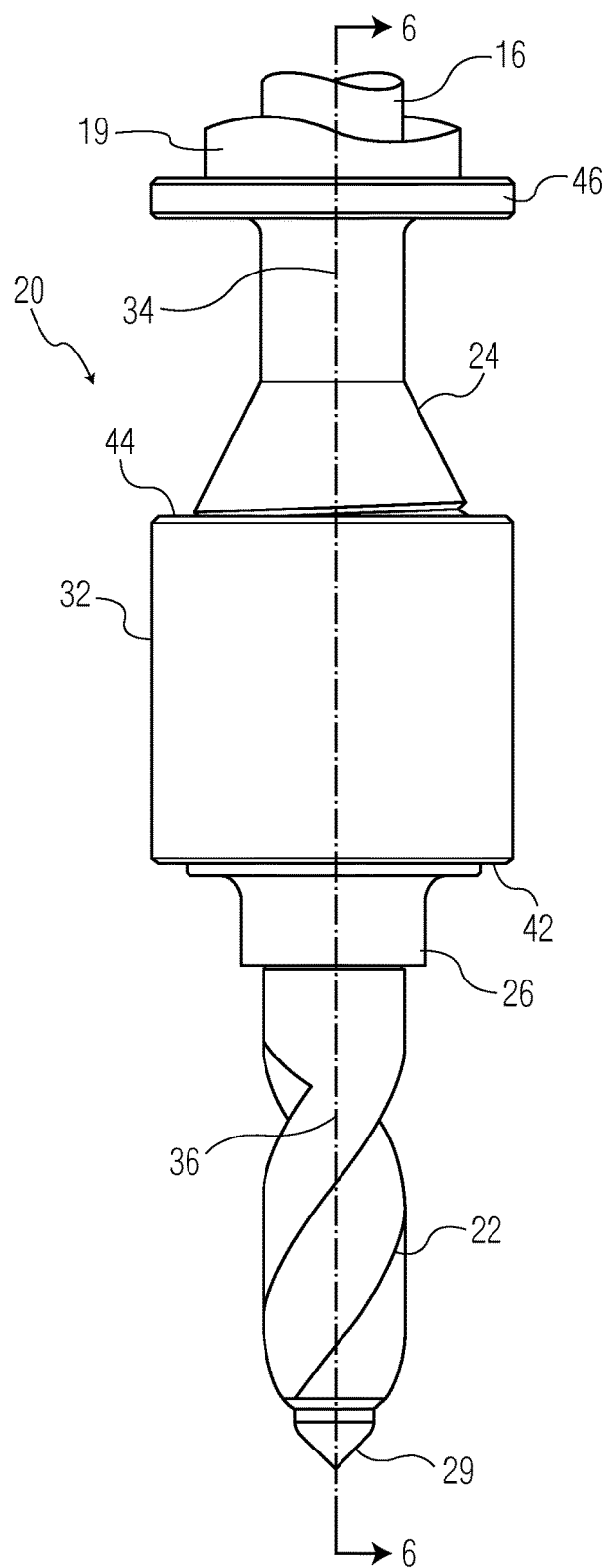
FIG. 3 is a view of FIG. 2 with the sleeve of the connecting device in a second position.
Figure 4:
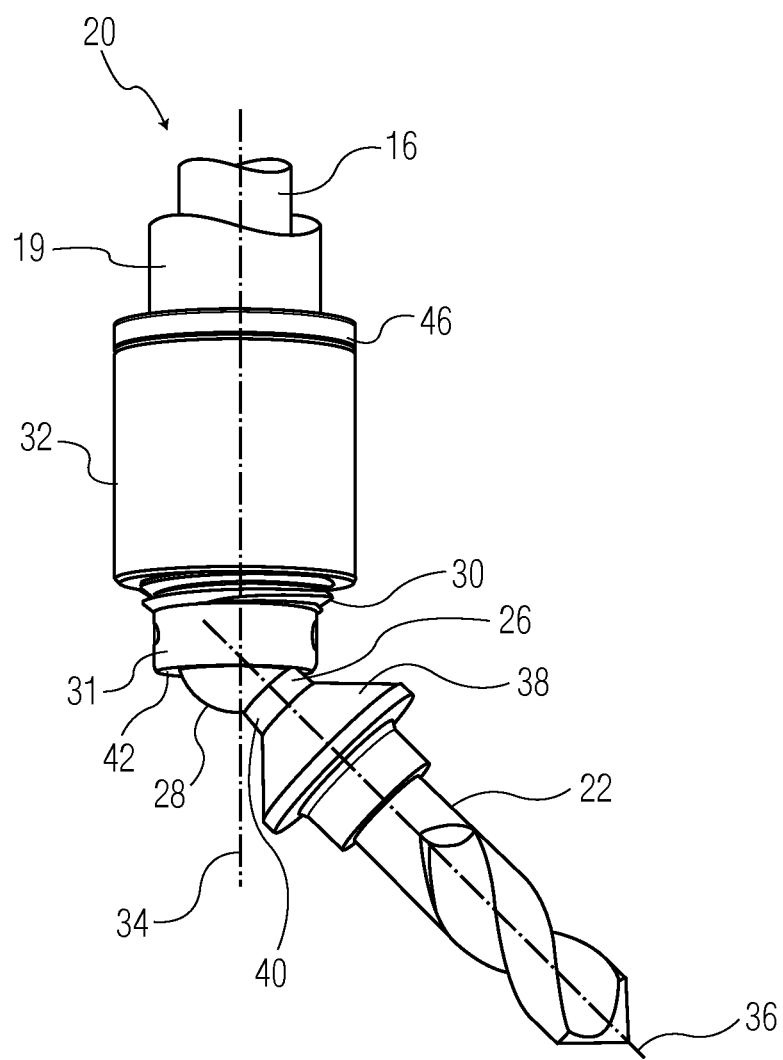
FIG. 4 is a view of the connection device of FIG. 2 with the sleeve in the first position and a drill rotated at an angle with respect to the drive axis of the tool.

Referring to FIGS. 2-4, there is shown an enlarged view of connecting element 20, which includes a first member 24 which is fixed to shaft 16 for rotation therewith, a second member 26, which includes a first end having drill bit 22 mounted thereon and a second end including a part-spherical joint portion 28. First member 24 includes a threaded portion 30 on an outer surface 31. A sleeve 32 is threadably mounted on threads 30. Thus, rotation of sleeve 32 in one direction advances the sleeve along a first longitudinal axis 34 toward second member 26. Rotation of sleeve 32 in the other direction moves the sleeve towards shaft 16. As seen in FIG. 4, second member 26 can be pivoted with respect to first member 24 such that a second longitudinal axis 36 thereof forms an angle with axis 34 of first member 24. Axis 34 is also the rotational axis of the driveshaft 16.

As sleeve 32 is rotated in a first direction it engages an outwardly angled surface 38 of second member 26. Angled surface 38 may be a frustro-conical section extending at approximately a 45° angle outwardly from part-spherical portion 28 toward a tip 29 of drill bit 22 of second member 26. As sleeve 32 is rotated in the first direction and advances it will contact surface 38. The advance of sleeve 32 on threads 30 may be continuous or if a detent system is used may be in increments of, for example, 5°. As sleeve 32 advances the angle between axes 34 and axes 36 is reduced until, as shown in FIG. 3, the axes are co-linear.

The maximum angle between axes 36 and axes 34 is limited by the contact of a cylindrical portion 40 of second member 26 and a rim 42 which surrounds a cavity 52 (best seen in FIG. 6) within first member 24. Typically, the maximum angle between axes 34 and 36 is between about 30 and 45°. Of course, this maximum angle can only occur when sleeve 32 is rotated in a second direction opposite from the first direction to be spaced from angled surface 38 so that portion 40 of second member 26 contacts rim 42. This second direction rotation of sleeve 32 is limited by the contact of an upper surface 44 of sleeve 32 against a stop plate 46, which is integrally formed with first member 24. Upon full rotation in the first direction of sleeve 32 an end 48 thereof contacts angled surface 38 as will be described in more detail below.

Figure 5:
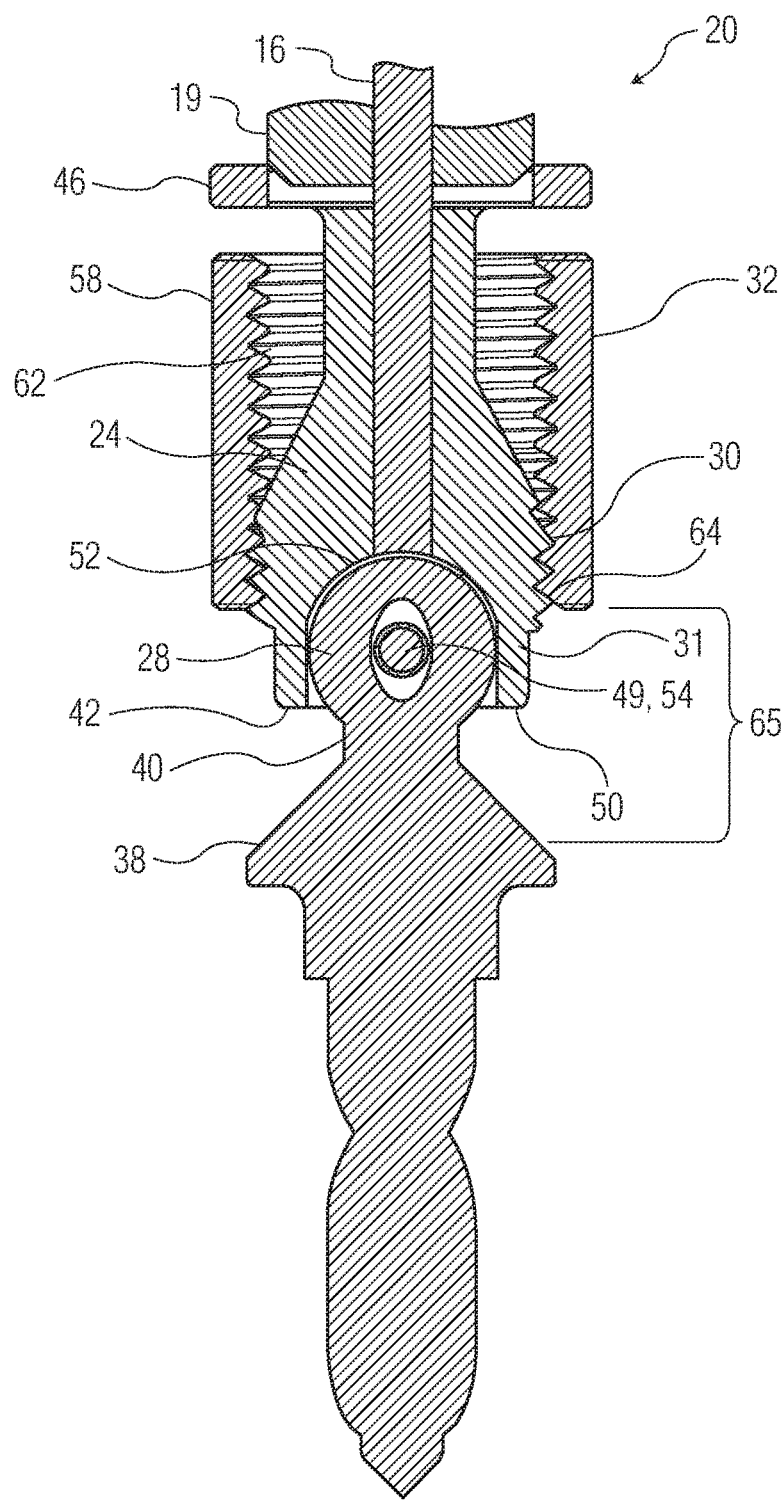
FIG. 5 is a cross-sectional view of the drive end connection device of FIG. 2 along line 5-5.
Figure 6:
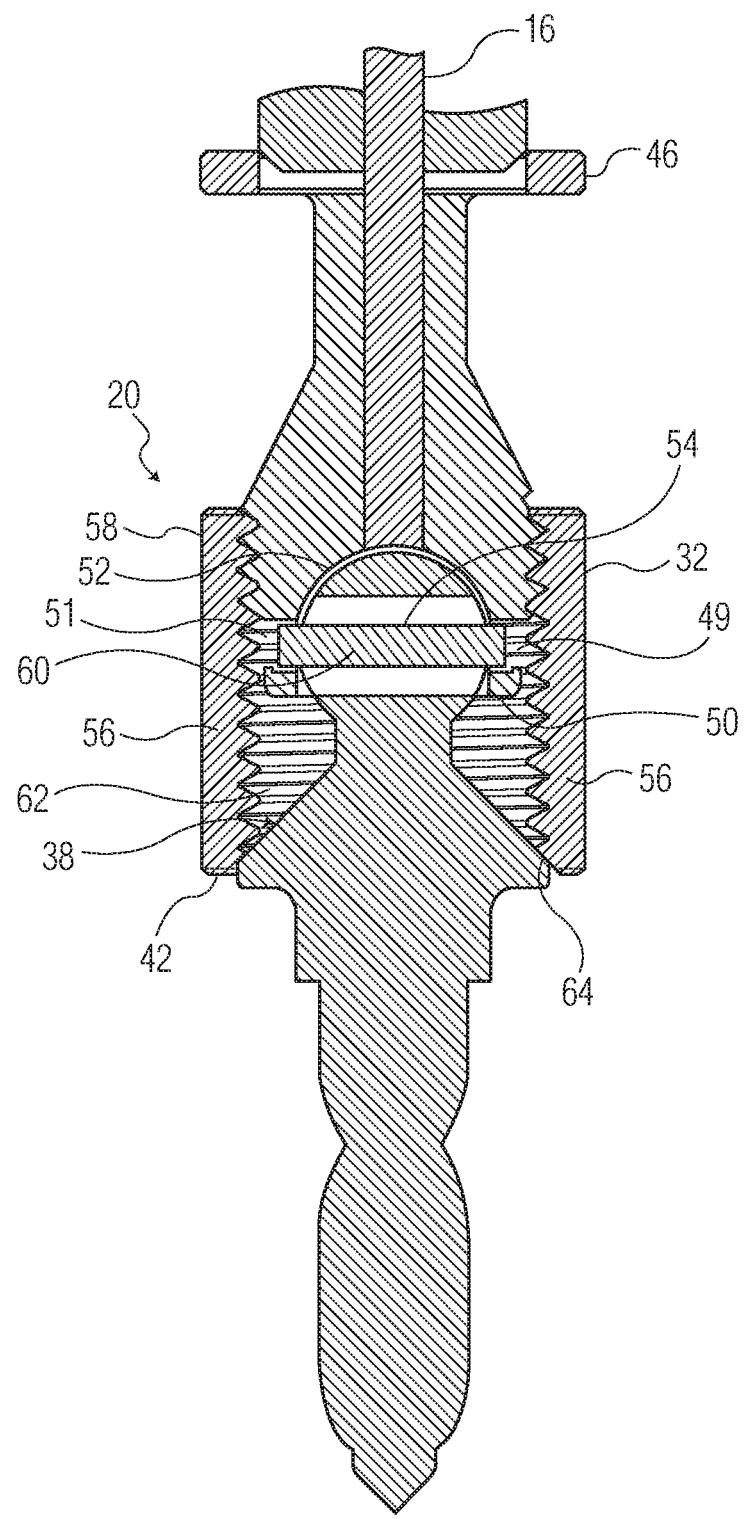
FIG. 6 is a cross-sectional view of the connection device of FIG. 3 along lines 6-6.

Referring to FIGS. 5 and 6, there is shown cross-sectional views of the connecting element 20. The cross-sectional views show the threading 50 on an inner surface of sleeve 32, which threading 50 engages threading 30 on the outer surface 31 of first member 24. In addition, in FIG. 6, there is shown cavity 52 internal to first member 24. Cavity 52 is preferably part-spherical and forms a socket for receiving part-spherical joint portion on second member 26. Cavity 52 and the outer surface 31, which includes threaded portion 30, define a wall through which a pair of holes 49 and 51 extend. Holes 49 and 51 receive a pivot pin 54, which extends through cavity 52.

Referring to FIGS. 5-9, there is shown second member 26 with part-spherical joint portion 28 having a bore 60 therethrough for receiving pivot pin 54. During manufacture of connecting element 20, sleeve 32 is threadably attached to first member 24 and moved into contact with stop member 46. Then part-spherical head 28 is inserted into part-spherical cavity 52 of FIG. 6 with hole 60 aligned with the holes or bores 49 and 51 in first member 24. Pin 54 is then inserted through the aligned bores 49, 51, and 60 and spot welded or otherwise permanently fixed within bores 49 and 51 of first member 24. This allows second member 26 to pivot around pin 54 and allows pin 54 to drive second member 26 as drive shaft 16 is driven.

As can be seen in FIGS. 5 and 6, sleeve element 32 includes an annular wall 56 which extends between an outer surface 58 thereof and inner threaded portion 50, which walls define an opening 62, which includes an inner tapered contact surface 38 designed to contact angled surface 64. Surfaces 38 and 64 may have the same angle. As shown in FIG. 5, when sleeve 32 is at its maximum location achieved by the rotation thereof in the first direction, axes 34 and 36 are coaxial, that is, at a 0° angle, and surface 64 is adjacent a lower end of frustro-conical surface 38. As the sleeve 32 is rotated in the second direction, a gap 65 occurs between angled surface 38 and tapered surface 64 of sleeve 32 so that some angular rotation of axis 36 of second member 26 is possible with respect to axis 34 of first member 24. This angle, or gap size, can be very finely adjustable depending on the pitch of threads 30 and 50, thus allowing a continuously variable limit on the angulation between axes 34 and 36 from 0° to 45°. As stated above, the maximum angle at any given location of sleeve 32 is determined by the contact of rim 42 of first member 24 and cylindrical surface 40 of member 26. Locking at 0° occurs when sleeve 32 is moved a sufficient distance toward and tapered surface 64 of angled surface 38.

Figure 7:
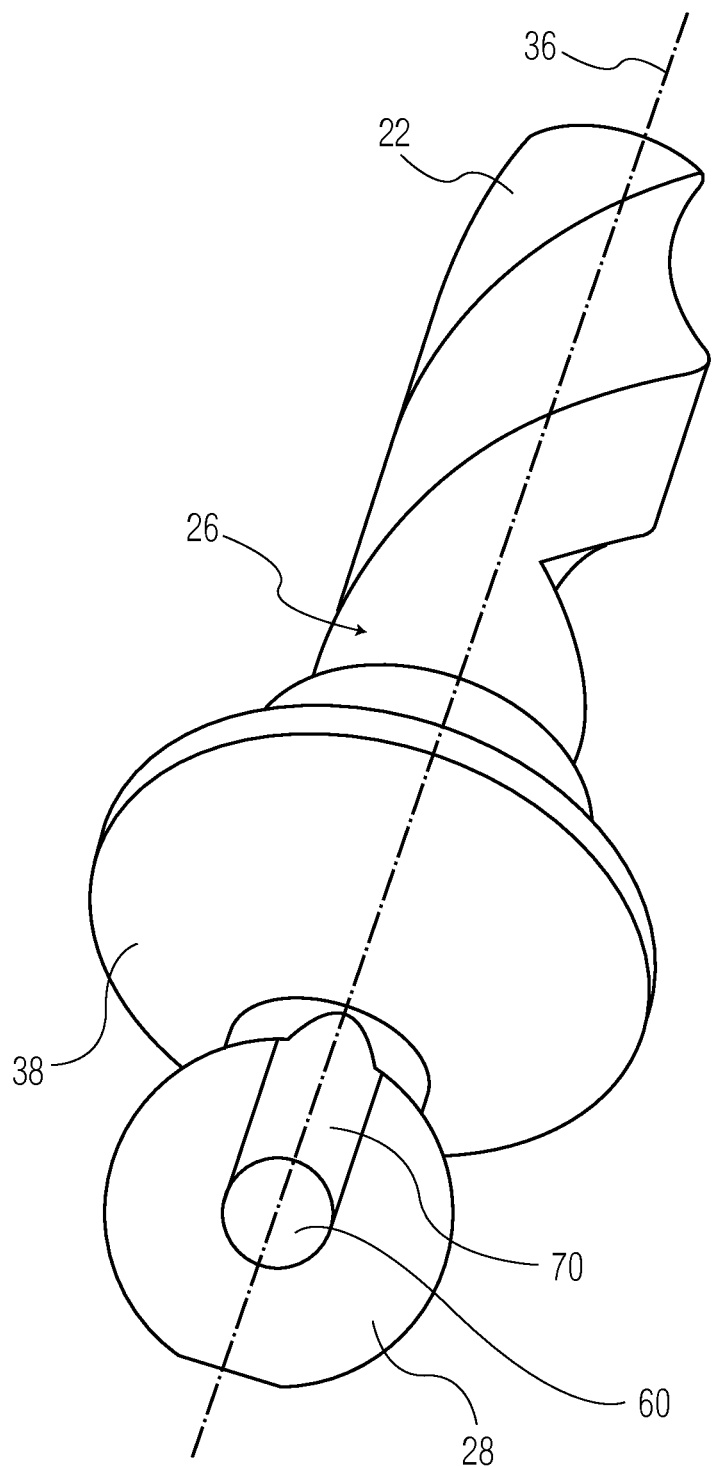
FIG. 7 is an isometric view of the second element of the connection element.
Figure 8:
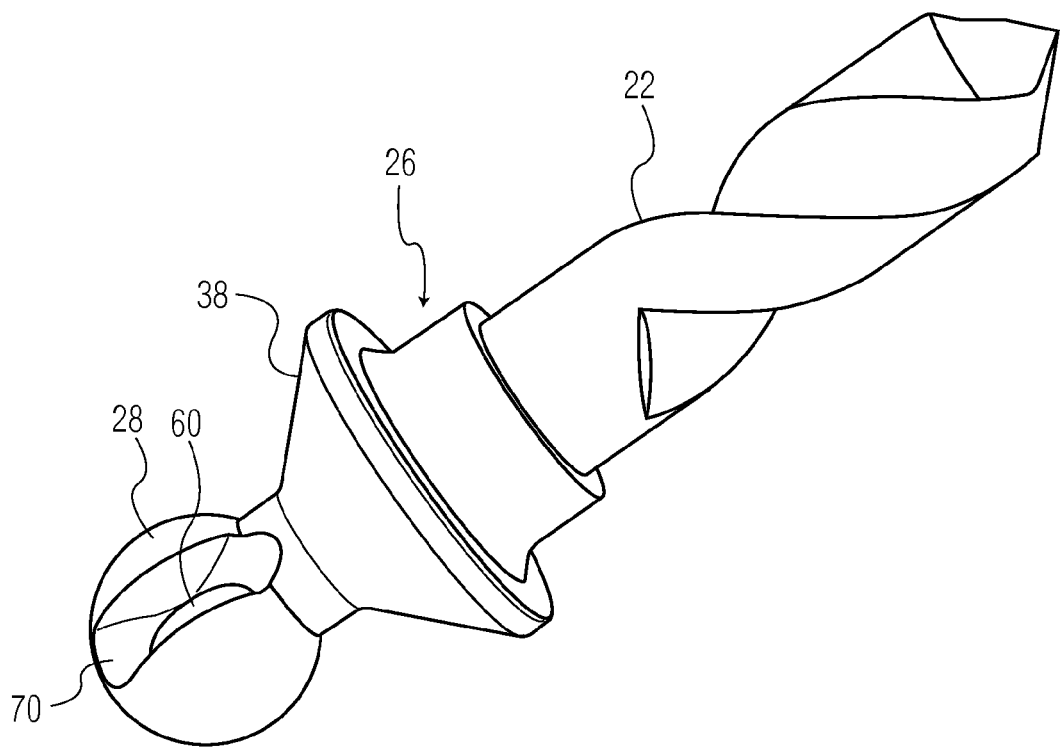
FIG. 8 is a second isometric view of the second member of the connection element.
Figure 9:
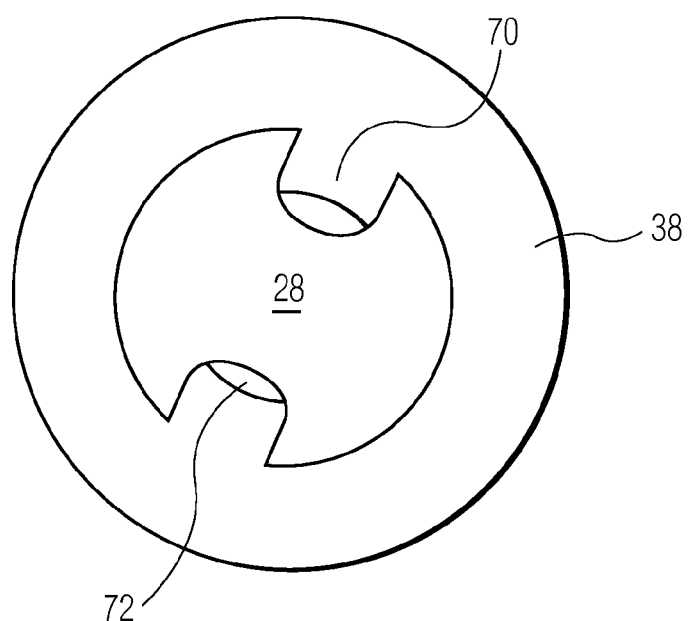
FIG. 9 is a top view of the second member of the connection element shown in FIGS. 7 and 8.

As best seen in FIGS. 7-9, part-spherical joint portion 28 of second member 26 includes a pair of grooves 70 and 72, which intersect hole 60 and extend parallel to axis 36 of second member 26. Grooves 70 and 72 allow limited rotation of second member 26 in a direction parallel to the axis of pivot pin 54. The rotation allowed in this direction is sufficient to obtain the maximum angle, for example, 45° or even up to 90° which may be attainable with use of bevel gears.

While the connecting element 20 can be used with the angle between axes 34 and 36 set by the sleeve 32 location to any desired angle such as, for example, between 0 and 45°, it can also be utilized to vary the angle during use such as during the drilling operation. In this case, such as during drilling a bore in bone, the operator or surgeon would initially set the maximum angle by locating sleeve 32 in a desired position along axis 34 toward drive shaft 16 and then, after drilling is initiated, gradually rotate sleeve 32 clockwise thus advancing the sleeve and rim 48 and its inner tapered surface 64 against angled surface 38 of second element 26 to gradually reduce the maximum angle until, if desired, the angle is 0°. This is advantageous because, as discussed above, as the angle decreases the component of applied force not acting in-line with the drive axis decreases so that more force can be applied to drilling the bore.

Figure 10:
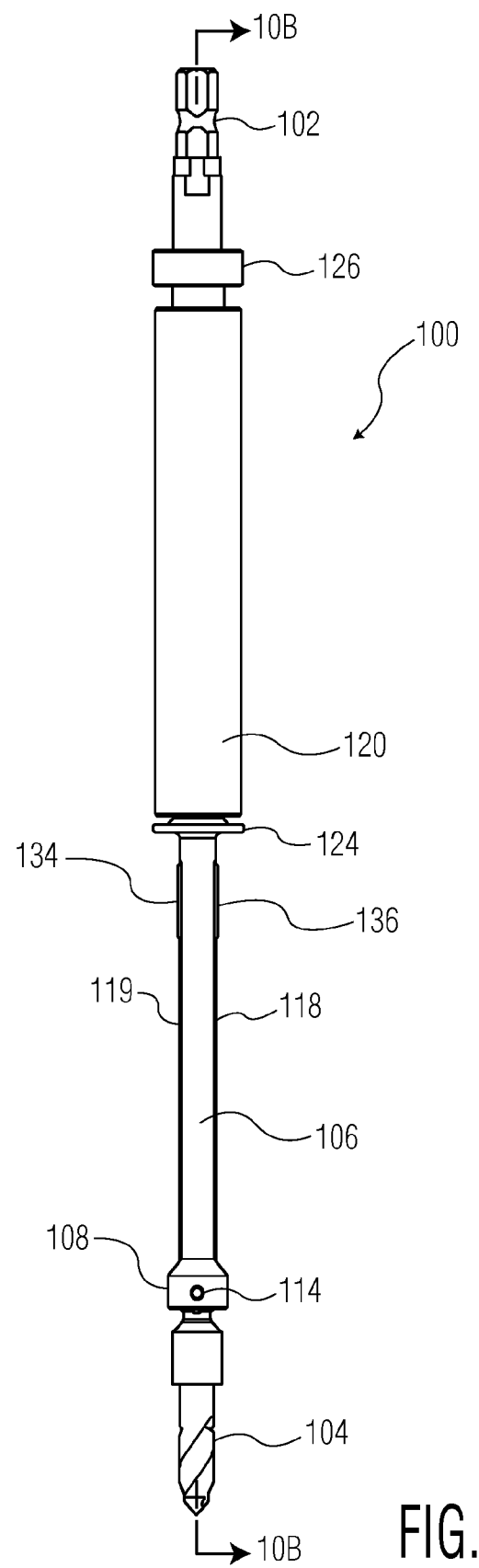
FIG. 10 is an elevation view of an alternate drive tool with a second design angled connector.

A second embodiment of the tool is shown in FIGS. 10-15. Referring to FIGS. 10-10C, there is shown an alternate embodiment of the driver tool 10 of the present invention generally denoted as 100. Driver tool 100 includes a power input drive end 102 and a drive element 104 which may be a drill or a screw driving bit of any known design. Tool 100 further includes a tubular shaft 106 extending along a central longitudinal axis 105 which includes a connector 108 at a first end with the power input drive end 102 at a second end of tool 100. Tubular shaft 106 has an inner bore 107. Drive element 104 includes a part-spherical head 110 which has a bore therethrough 112 for receiving pivot pin 116 which design is in many respects is the same as the head and bore described above with respect to the first embodiment of the drive tool 10. Connector element 108 includes a bore 117 which receives pivot pin 116. Pivot pin 116 may be rigidly fixed with respect to element 108, i.e., not rotate in bores 117. Again, this is similar to that described above with the first embodiment of the drive tool 10.

In the second embodiment 100, the sleeve or ferrule 18 of FIG. 1A is eliminated and a pair of deflectable fingers, arms or tabs 118 and 119 are used to maintain the drive element 104 at least temporarily in a desired angled position. Arms or tabs 118, 119 are each mounted between a first slots 150 and a second slot 152 formed on opposite sides of the drive shaft 106. In other words, each deflectable arm or tab 118 and 119 is located between a slot 150 and a slot 152 as shown in FIGS. 13-15.

Figure 10A:
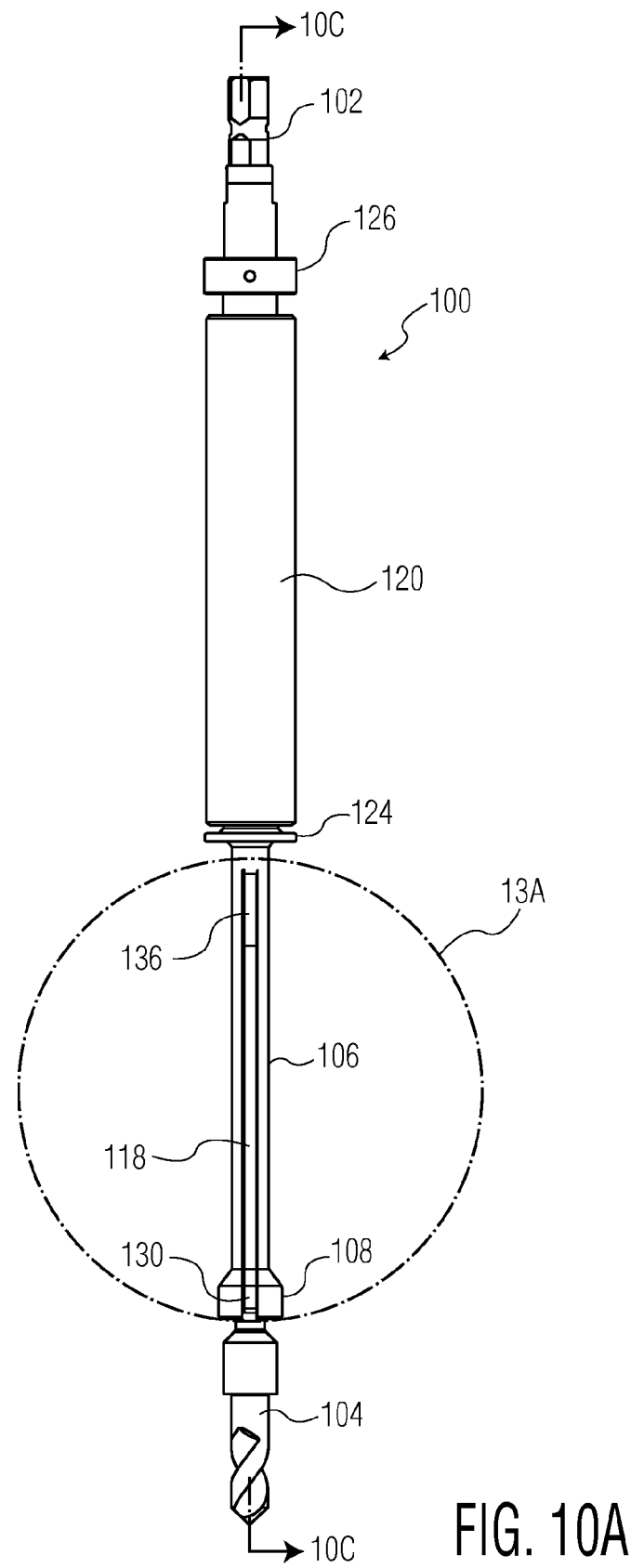
FIG. 10A is the drive tool of FIG. 10 with the shaft rotated 90° about the longitudinal axis from the position shown in FIG. 10.
Figure 10B:
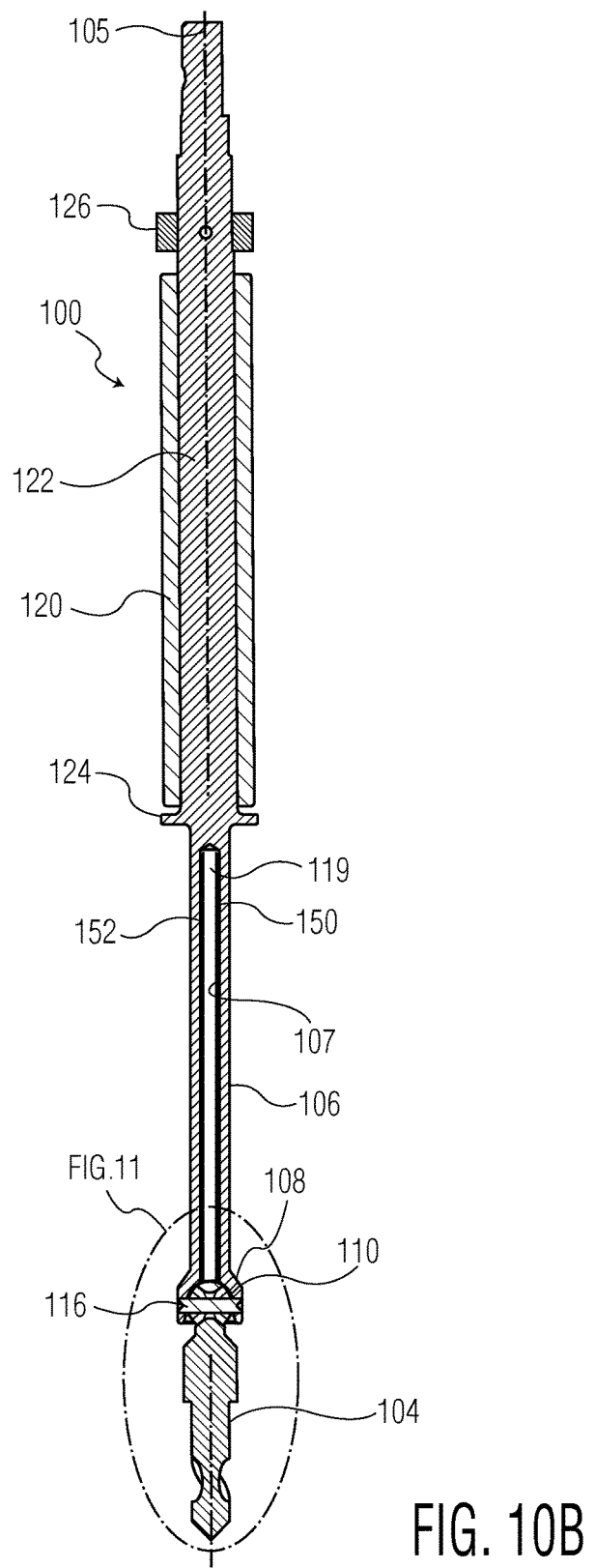
FIG. 10B is a cross-sectional of FIG. 10 along the lines of 10B-10B.
Figure 10C:
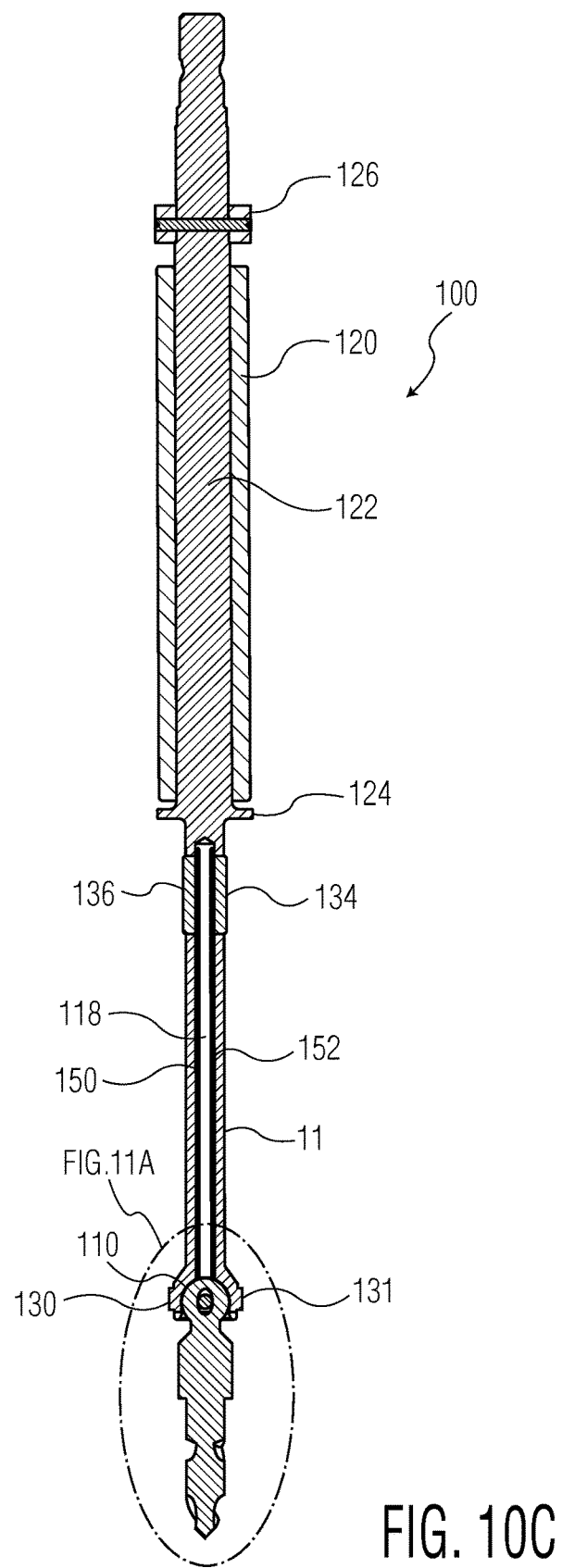
FIG. 10C is a cross-sectional of FIG. 10A along lines 10C-10C.
Figure 11:
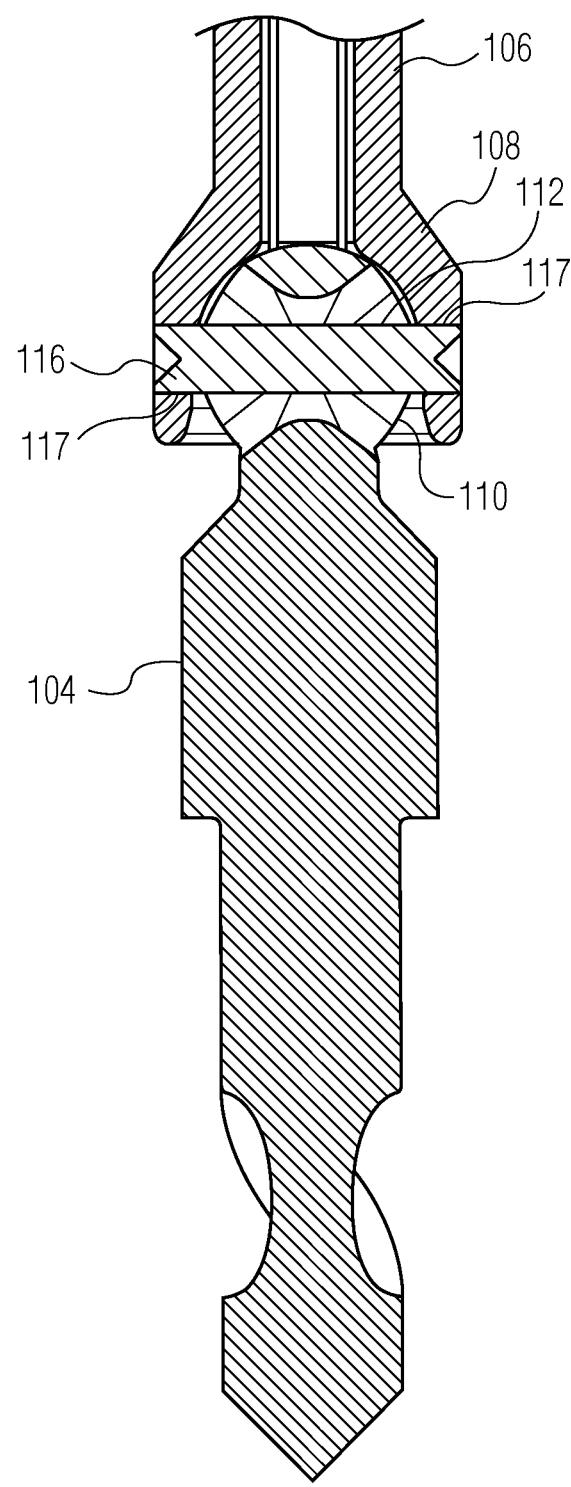
FIG. 11 is an enlarged view of the tip of FIG. 10B
Figure 11A:
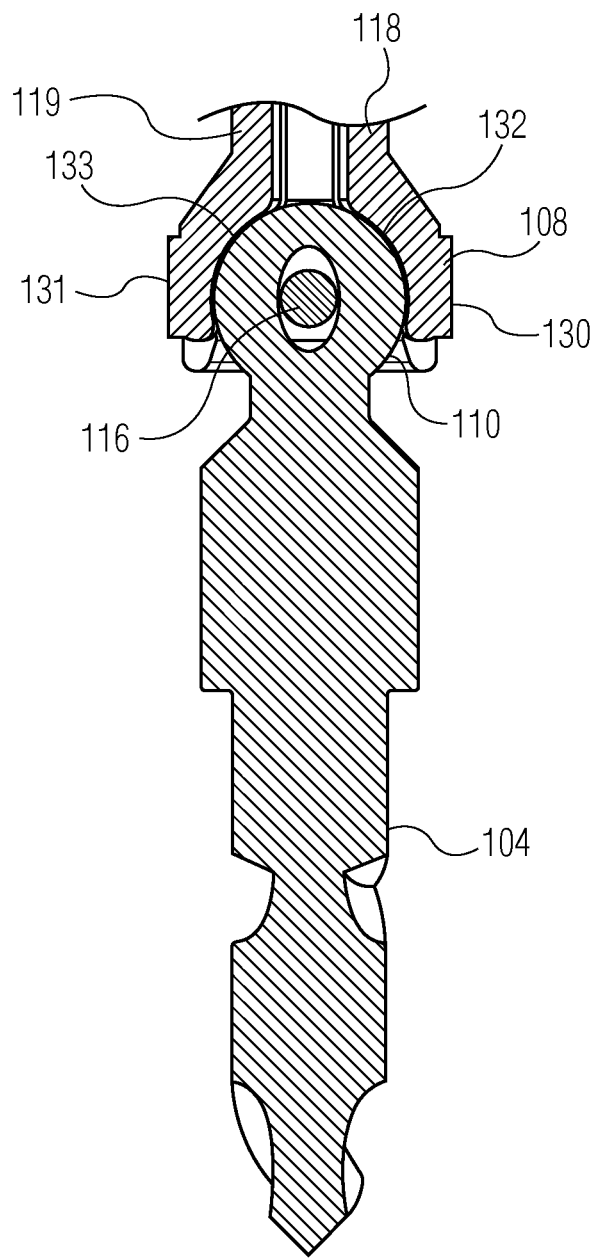
FIG. 11A is an enlarged view of the tip of FIG. 10C, including the connection element and a drive element.
Figure 12:
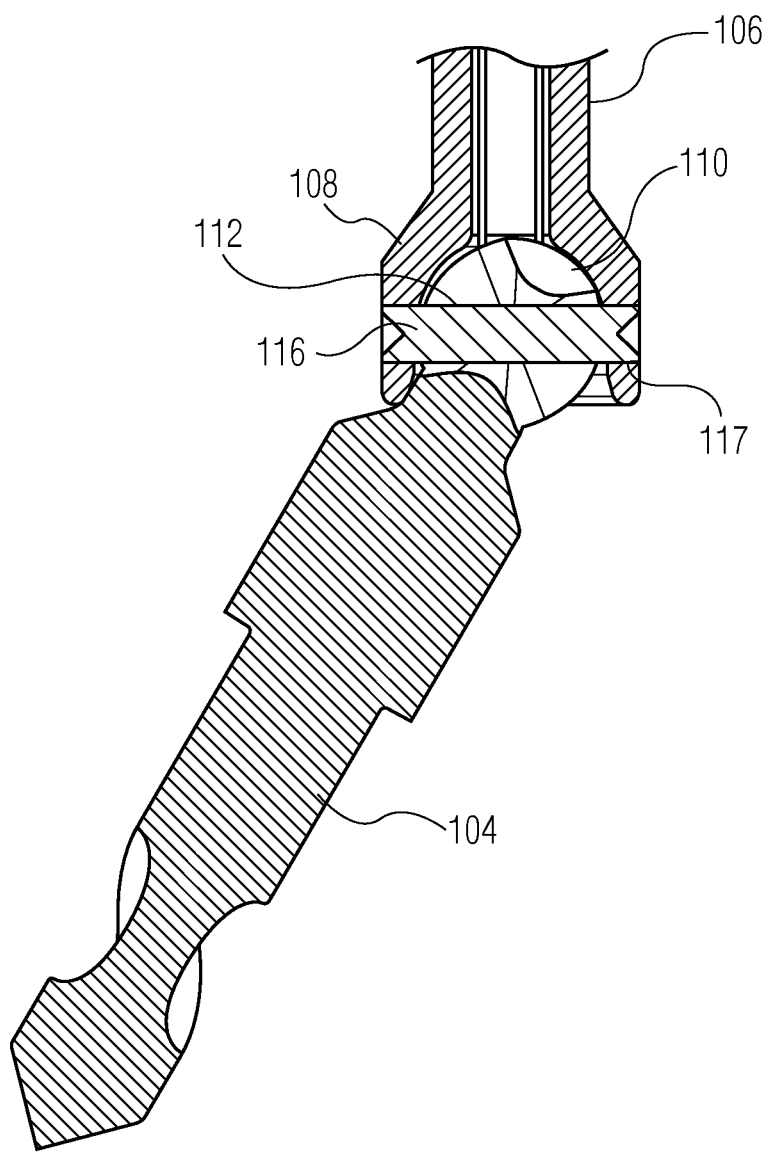
FIGS. 12 and 12A show the connector portion of the drive shaft including the drill element angled with respect to the longitudinal axis of the drive shaft.
Figure 12A:
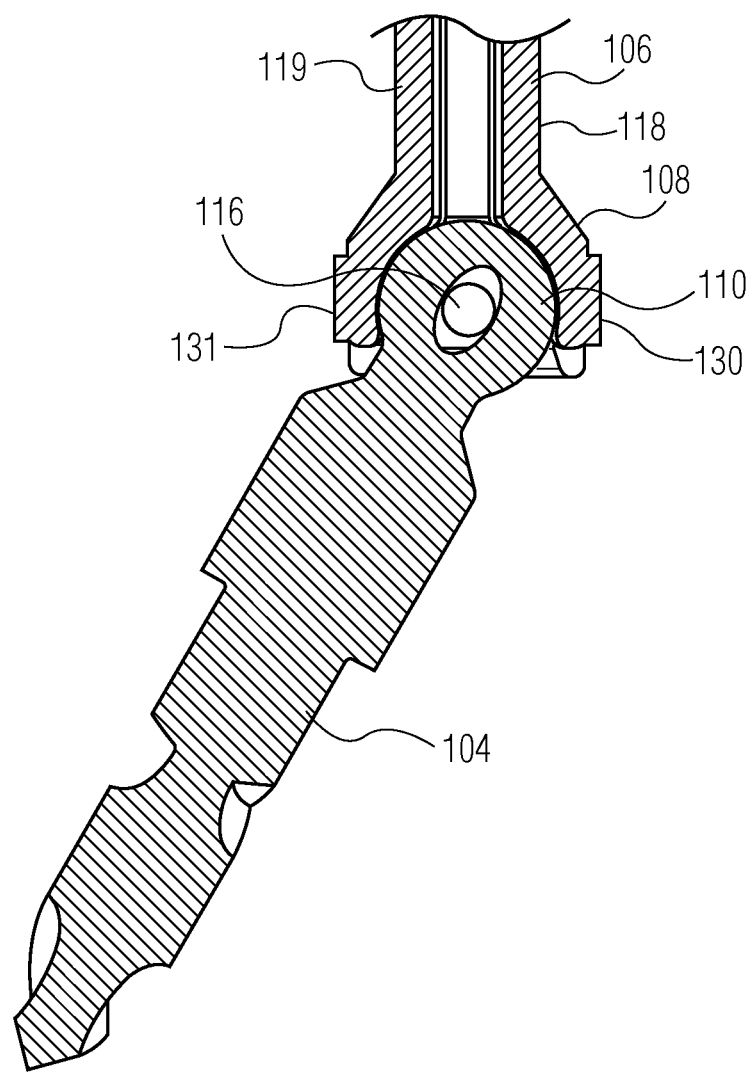

Referring to FIGS. 11-12A, there is shown an enlarged connector and drive element end of the cross-sections of FIGS. 10B and 10C along lines 10B-10B of FIGS. 10 and 10C-10C of FIG. 10A respectively. Also shown in FIGS. 10-10C there is a handle portion 120 which allows the drive shaft upper portion 122 to be held by the surgeon allowing the shaft 106 including portion 122 to rotate while handle 120 is maintained non-rotatable. A flange 124 and a stop element 126 are mounted on shaft portion 122 to maintain the axial position of handle 120 on shaft portion 122.

Figure 13:
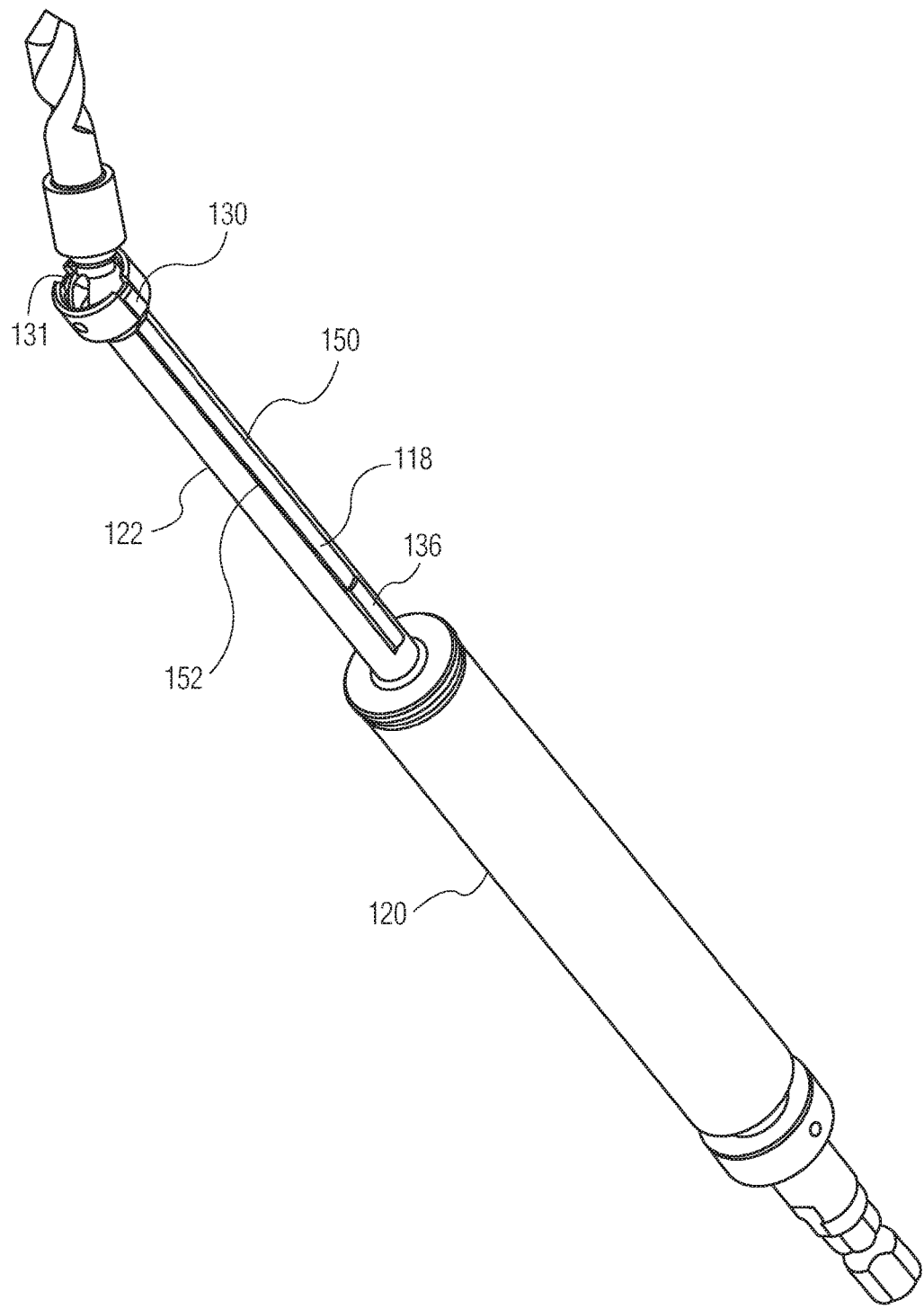
FIG. 13 is an isometric view of the drive tool of the present invention with the drill element angled with respect to the drive shaft longitudinal axis.
Figure 14:
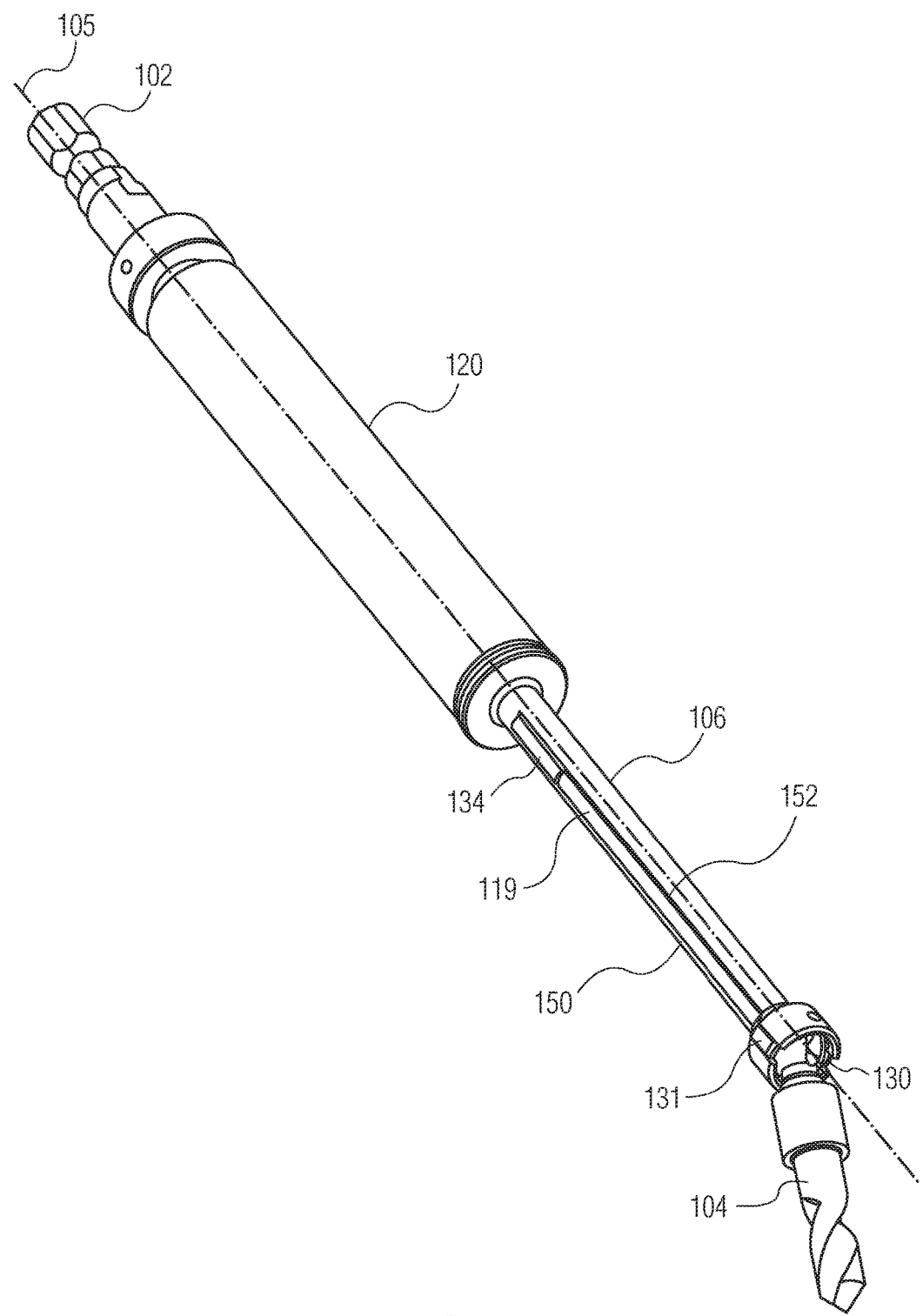
FIG. 14 is a second isometric view of the drive tool similar to that show in FIG. 13.
Figure 15:
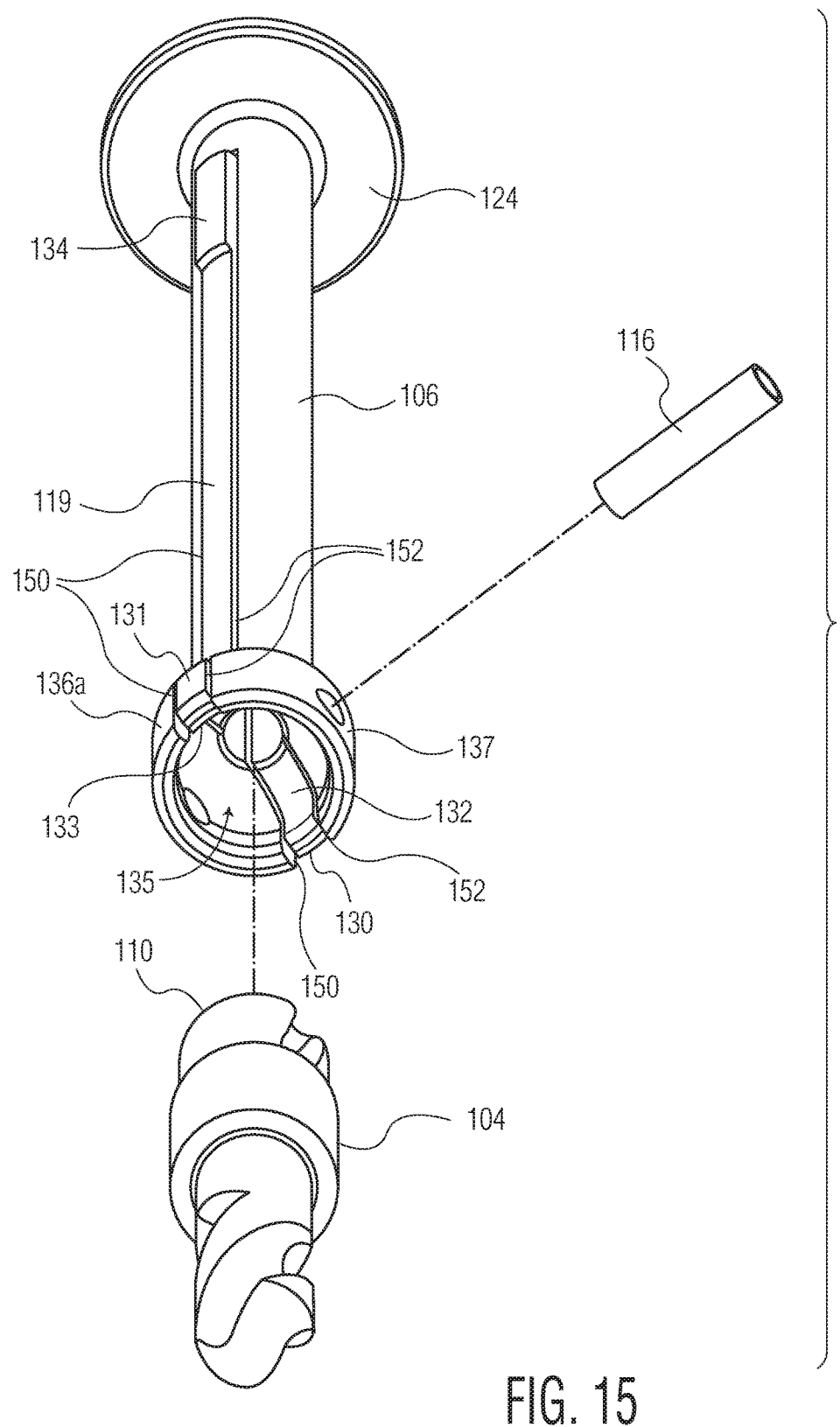
FIG. 15 is an exploded view of the leading end of the drive tool shown in FIGS. 10-14.

As can be seen in FIGS. 13-15, each arm or tab 118, 119 includes first raised end portions 130, 131 which have inner surfaces 132 and 133 respectively which are concave or part-spherical in shape to match the part-spherical outer surface of head 110 of drive element 104. Inner surfaces 132 and 133 form part of a concave or part-spherical cavity 135 surrounded by walls 136a and 137 which have outer surfaces which may form part of a cylinder. As best seen in FIG. 15, the deflectable arms 119, 120 have second raised portions or buttons 134, 136 formed on shaft 106 between each pair of slots 150, 152, and extending outwardly therefrom. First and second raised portions 134, 136 can be squeezed by the surgeon to engage the inner surfaces 132, 133 on the head 110 of drive element 104. This contact creates friction to hold the drive element 104 in an angular position.

Figure 13A:
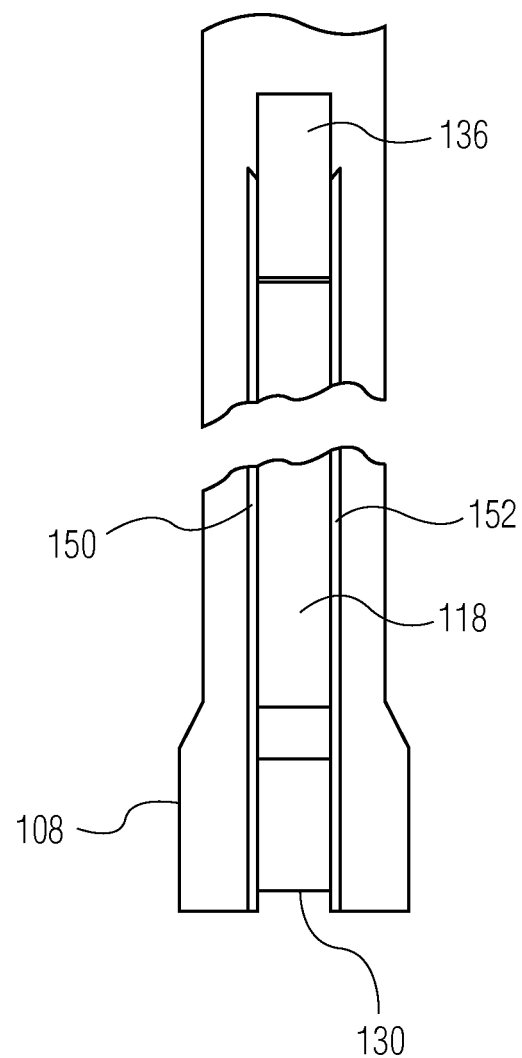
FIG. 13A is an enlarged partial view of the Electro discharged machined shaft portion of FIG. 10A.

Preferably, arms 118 and 119 are formed by wire EDM (Electro Discharge Machining) into the tubular drive shaft portion 106 to form the first and second pair of slots 150 and 152 formed on opposite sides of tubular portion 106 on either side of arms 118 and 119. Thus a first pair of slots 150, 152 define arm 118 (as shown in FIG. 13A), and a second pair of slots 150, 152 define arm 119. This is done by bringing the single wire EDM electrode into contact with the opposing sides of the end of tubular portion 106 and moving the electrodes parallel to axis 105 of the shaft towards power input drive end 102 to make a first linear cut forming slot 150, and then withdrawing the electrode and moving the wire EDM electrode around the circumference a predetermined circumferential distance and reinserting it and then moving toward connector 104 to make the second longitudinal cut forming slot 152 parallel to axis 105. Both the thickness of the tubular portion 106 between an outer surface thereof and inner bore 107 and the circumferential spacing of the two linear cuts forming slots 150, 152 determine the flexibility of arms 118 and 119. FIG. 13A shows the end result described above including the slots 150 and 152 formed by the electrode.

It is possible to permanently bend arms or tabs 118, 119 inwardly so that there is always some friction force generated against head 110 to hold drive element 104 in any desired angled position which force can then be increased by depressing both raised button portions 134, 136. It is also possible to shorten the length of the wire EDM cuts 150 and 152 along shaft portion 106, and even have the cuts only in the area of the connection element 108 and thus use raised portions 130, 131 to generate additional force on head 110 when squeezed by the surgeon.

While the preferred method is to use wire EDM, the arms, fingers or tabs could be formed on drive shaft portion 106 in any convenient manner, as long as they can be inwardly deflected. Therefore slots could be cut along shaft portion 106 by a saw or machine tool and the fingers, arms or tabs could be attached by welding or riveting.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A drive tool comprising:
 a tubular drive shaft extending along a first axis having a first end defining a connector element including a part-spherical cavity and a second drive element end, the connector element having walls surrounding the part-spherical cavity, and a first and second pair of slots extending along the tubular drive shaft and the walls of the connector element between an outer surface of the connector element and the part-spherical cavity;
 a pivot member extending along a second axis having a tool at a first end and a part-spherical head at a second end, the head pivotally mounted in the part-spherical cavity in the connector element;
 first and second deflectable arms engageable with the part-spherical head are mounted on the tubular drive shaft adjacent the cavity of the tubular drive shaft and deflectable through the respective first and second pair of slots into engagement with the part-spherical head;
 wherein the first and second pair of slots of the tubular drive shaft respectively surround the first and second deflectable arms and extend parallel to the first axis, have a first end at the connector element cavity and wherein the arms are mounted on the tubular drive shaft at a second end of the slots, the second end of the slots being closer to the second end of the tubular drive shaft than the first end of the tubular drive shaft; and
 wherein each arm has a first raised portion extending outwardly of an outer surface of the tubular drive shaft, each raised portion located between the first and second pair of slots surrounding the respective deflectable arm.

2. The drive tool as set forth in claim 1 wherein the part-spherical head of the pivot member includes a bore therethrough along a second axis perpendicular to the first axis and a pivot pin mounted on the walls of the connector element surrounding the cavity extends through the bore in the part-spherical head along an axis generally perpendicular to the first axis.

3. The drive tool as set forth in claim 2, wherein the bore in head has a pair of grooves extending from the bore to allow the head to be rotated about an axis transverse to the axis of the pin.

4. The drive tool as set forth in claim 1, wherein the first and second pair of slots are diametrically opposed on the tubular drive shaft.

5. The drive tool as set forth in claim 1, wherein a first end of each deflectable arm has a part-spherical inner surface conforming in shape to the part-spherical head of the pivot member.

6. The drive tool as set forth in claim 5 wherein the first raised portion is located adjacent the second end of the first and second pair of slots and has a second raised portion on the first and second deflectable arms and the second raised surface portion extending outwardly of the outer surface of the tubular drive shaft spaced from the first raised portion along the tubular drive shaft first axis.

7. The drive tool of claim 6 wherein the second raised portion is located on the first and second defletable arm adjacent the first end of the respective first and second pair of slots.

8. The drive tool as set forth in claim 1, wherein each deflectable arm has an inner surface conforming to the part-spherical shape of the pivot element head.

9. A drive tool comprising:
 a tubular drive shaft extending along a first axis having a first end defining a connector element including a part-spherical cavity and a second driver end, the connector element having walls surrounding the part-spherical cavity, and a first and second pair of slots extending along the tubular drive shaft and along the walls of the connector element between an outer surface thereof and the part-spherical cavity;
 a pivot member extending along a second axis having a tool at a first end and a part-spherical head at a second end, the head pivotally mounted in the part-spherical cavity in the connector element;
 first and second deflectable arms engageable with the part-spherical head are mounted adjacent the cavity of the tubular drive shaft and are respectively surrounded by and deflectable through the first and second pair of slots onto the part-spherical head;
 wherein the first and second pair of slots of the tubular drive shaft extend parallel to the first axis and extend through the walls of the connector element of the tubular drive shaft first end and wherein the arms are fixedly mounted at a second end of the slots, the second end of the slots closer to the second drive end of the tubular drive shaft than the first end of the tubular drive shaft; and
 wherein each arm has a first and a second raised portion axially spaced along the first axis and extending outwardly of an outer surface of the tubular drive shaft, each raised portion located between the first and second pair of slots surrounding the respective first and second deflectable arm.

10. The drive tool as set forth in claim 9, wherein a first end of each deflectable arm has a part-spherical inner surface conforming in shape to the part-spherical cavity in the connector element.

11. The drive tool as set forth in claim 9, wherein each deflectable arm has the first raised portion extending outwardly of the outer surface of the walls of the connector element.

12. The drive tool as set forth in claim 11 wherein each deflectable arm has the second raised surface portion at the second end of each pair of slots extending outwardly of an outer surface of the tubular drive shaft.

13. The drive tool as set forth in claim 9, wherein adjacent the part-spherical cavity each deflectable arm has an inner surface conforming to the shape of the part-spherical shape of the pivot element head.

14. A drive tool comprising:
a tubular drive shaft extending along a first axis having a first end defining a connector element including a part-spherical cavity and a second drive element end, the connector element having walls surrounding the part-spherical cavity, and a first and second pair of slots extending along the tubular drive shaft and through the walls of the connector element between an outer surface of the connector element and the part-spherical cavity;
a pivot member extending along a second axis having a tool at a first end and a part-spherical head at a second end, the head pivotally mounted in the part-spherical cavity in the connector element;
first and second deflectable arms engageable with the part-spherical head are mounted on the tubular drive shaft adjacent the cavity of the tubular drive shaft and respectively deflectable through the first and second pair of slots into engagement with the part-spherical head;
wherein the first and second pair of slots of the tubular drive shaft respectively surround both the first and second deflectable arms and extend parallel to the first axis and through the connector element cavity walls at a first end of each pair of slots and wherein the arms are mounted on the tubular drive shaft at a second end of the slots, the second end of the slots being closer to the second end of the tubular drive shaft than the first end of the tubular drive shaft;
wherein each arm has a first raised portion adjacent the first end of the first and second pair of slots extending outwardly of an outer surface of the tubular drive shaft; and
wherein the part-spherical head of the pivot member includes a bore therethrough along a second axis perpendicular to the first axis and a pivot pin mounted on the walls of the connector element surrounding the cavity extends through the bore in the part-spherical head along an axis generally perpendicular to the first axis.

15. The drive tool as set forth in claim 14 wherein each deflectable arm has a second raised portion extending outwardly of an outer surface adjacent the first end of the first and second pair of slots.

16. The drive tool of claim 14 wherein a second raised portion is located on the first and second deflectable arms adjacent the first end of the respective first and second pair of slots.

* * * * *